United States Patent [19]
Camp

[11] Patent Number: 5,997,892
[45] Date of Patent: Dec. 7, 1999

[54] TOPICAL THERAPEUTIC COMPOSITION FOR AND METHOD OF TREATING PSORIASIS

[76] Inventor: Gary Don Camp, 704C Ryo Mountain Loop, Fairmout, Ga. 30139

[21] Appl. No.: 09/159,174

[22] Filed: Sep. 23, 1998

Related U.S. Application Data

[60] Provisional application No. 60/061,468, Oct. 9, 1997.

[51] Int. Cl.⁶ .......................... A61K 7/00; A61K 33/04; A61K 31/60; A61K 31/355
[52] U.S. Cl. .......................... 424/401; 424/705; 514/159; 514/458; 514/859; 514/863
[58] Field of Search .................................. 424/401, 705; 514/159, 458, 859, 863

[56] References Cited

U.S. PATENT DOCUMENTS

| | | | |
|---|---|---|---|
| 4,944,939 | 7/1990 | Moore | 424/73 |
| 5,338,535 | 8/1994 | Berndt | 424/69 |
| 5,607,980 | 3/1997 | McAtee et al. | 514/476 |
| 5,652,228 | 7/1997 | Bissett | 514/77 |

Primary Examiner—Shelley A. Dodson
Assistant Examiner—Marina Lamm
Attorney, Agent, or Firm—Eric R. Katz

[57] ABSTRACT

According to one embodiment of the topical therapeutic composition of the present invention, the composition comprises a combination of sulfur and Vitamin E in a range of about three parts of Vitamin E to one part sulfur to about equal parts of sulfur and Vitamin E. Preferably, the sulfur is in powder form, for example, sublimed sulfur, prior to mixing with the Vitamin E. The Vitamin E comprises either natural vitamin E (d-alpha tocopherol) or synthetic vitamin E (dl-alpha tocopherol) or a blend of both natural vitamin E (d-alpha tocopherol) and synthetic vitamin E (dl-alpha tocopherol).

16 Claims, No Drawings

TOPICAL THERAPEUTIC COMPOSITION FOR AND METHOD OF TREATING PSORIASIS

This application claims the benifit of 60/06/468 filed on Oct. 9, 1997.

FIELD OF THE INVENTION

The present invention generally relates to the treatment of skin conditions, and more particularly, to a topical therapeutic composition for and method of treating skin conditions such as dry skin, acne, or psoriasis.

BACKGROUND

Psoriasis is a common disease that affect may people. Hereditary factors are important. If one parent has psoriasis, the risk for the child is about 25% and if both parents have psoriasis there is a risk of about 60–70%. Drugs thought to precipitate or Worsen psoriasis include alcohol and, in some patients, beta-blocker and non-steroidal anti-inflammatory agents.

Psoriasis is characterized by thickened, erythematous, well-demarcated areas of skin covered by silvery scales. The extent of involvement ranges from isolated, small lesions to the whole body surface. There are several clinical forms of psoriasis and it change qualitatively from stable plaque lesions to an unstable form typified by eruptive inflammatory lesions.

Psoriasis is not a static disease: seasonal fluctuations, spontaneous remission, and physical and emotional well-being all affect the disease and hence its management. Most patients with localized, plaque-type psoriasis are able manage their disease at home with topical therapy with corticosteroid creams and ointments, which sometimes have serious side effects do to the action of the steroids. For more widespread forms, some form of phototherapy, either alone or combined with topical therapy is usually need. In resistant psoriasis, photo chemotherapy or systemic therapy may be indicated.

SUMMARY OF THE INVENTION

It is an object of the present invention to provide a topical therapeutic composition for the treatment of dry skin conditions.

It is a further object of the present invention to provide a method of using the topical therapeutic composition for the treatment of dry skin conditions, including psoriasis as well as acne.

One advantageous feature of the present invention is that the topical therapeutic composition is comprised of all natural ingredients.

Another advantageous feature of the present invention is that it provides an effect treatment for psoriasis.

DETAILED DESCRIPTION OF THE PREFERRED EMBODIMENT(S)

According to one embodiment of the topical therapeutic composition of the present invention, the composition comprises a combination of sulfur and Vitamin E in a range of about three parts of Vitamin E to one part sulfur to about equal parts of sulfur and Vitamin E. Preferably, the sulfur is in powder form, for example, sublimed sulfur, prior to mixing with the Vitamin E. The Vitamin E comprises either natural vitamin E (d-alpha tocopherol) or synthetic vitamin E (dl-alpha tocopherol) or a blend of both natural vitamin E (d-alpha tocopherol) and synthetic vitamin E (dl-alpha tocopherol). It should be understood by one of ordinary skill in the art that the amount of sulfur required need only be an effective about which provides the necessary therapeutic effect.

According to a further embodiment of the topical therapeutic composition of the present invention, the composition comprises a combination of sulfur and Vitamin E, in the range as described above, with the further addition of salicylic acid. One example for making this further embodiment of the topical therapeutic composition comprises mixing together about five (5) teaspoons of sulfur powder, for example, sublimed sulfur, about five (5) teaspoons of Vitamin E, for example, natural vitamin E (d-alpha tocopherol) or synthetic vitamin E (dl-alpha tocopherol) or blend of both natural and synthetic vitamin E and salicylic acid in the range of between about one quarter (¼) to about one (1) teaspoon.

Effective treatment of skin conditions, such as, for example, psoriasis or acne was achieved by applying the therapeutic composition to the affected area of the skin at least twice a day for at least three days to start to experience a therapeutic effect. Treatment is recommended to continue for a period of time ranging from about two weeks to a month.

Although the present invention has been described with particular reference to its preferred embodiments, it should be understood that many variations and modifications will now be obvious to those skilled in that art, and it is preferred, therefore, that the scope of the invention be limited, not by the specific disclosure herein, but only by the appended claims.

What is claimed is:

1. A topical therapeutic composition for the treatment of psoriasis, the composition consisting essentially of a combination of sulfur and Vitamin E in a range of about three parts of Vitamin E to about one part sulfur to about equal parts Vitamin E and sulfur.

2. A topical therapeutic composition according to claim 1, wherein the sulfur is powdered sulfur.

3. A topical therapeutic composition according to claim 2, wherein the powdered sulfur is sublimed sulfur.

4. A topical therapeutic composition according to claim 1, wherein the Vitamin E is selected from the group consisting of: natural vitamin E (d-alpha tocopherol), synthetic vitamin E (dl-alpha tocopherol) and mixtures thereof.

5. A topical therapeutic composition for the treatment of psoriasis, the composition consisting essentially of about five (5) parts sulfur; about five (5) parts Vitamin E; and about one quarter to one part salicylic acid.

6. A topical therapeutic composition according to claim 5, wherein the sulfur is powdered sulfur.

7. A topical therapeutic composition according to claim 6, wherein the powdered sulfur is sublimed sulfur.

8. A topical therapeutic composition according to claim 5, wherein the Vitamin E is selected from the group consisting of: natural vitamin E (d-alpha tocopherol), synthetic vitamin E (dl-alpha tocopherol) and mixtures thereof.

9. A method of treating psoriasis comprising the steps of:

applying a therapeutic composition consisting essentially of a combination of sulfur and Vitamin E in a range of about three parts of Vitamin E to about one part sulfur to about equal parts Vitamin E and sulfur to an area of the skin affected with psoriasis at least twice a day; and repeating the application of the composition, twice a day, for at least three days.

10. A method according to claim 9, wherein the sulfur of the composition is powdered sulfur.

11. A method according to claim 10, wherein the powdered sulfur is sublimed sulfur.

12. A method according to claim 9, wherein the Vitamin E of the composition is selected from the group consisting of: natural vitamin E (d-alpha tocopherol), synthetic vitamin E (dl-alpha tocopherol) and mixtures thereof.

13. A method of treating psoriasis according to claim 9, wherein the therapeutic composition consisting essentially of about five (5) parts sulfur; about five (5) parts Vitamin E; and about one quarter to one part salicylic acid.

14. A method according to claim 13, wherein the sulfur of the composition is powdered sulfur.

15. A method according to claim 14, wherein the powdered sulfur is sublimed sulfur.

16. A method according to claim 13, wherein the Vitamin E of the composition is selected from the group consisting of: natural vitamin E (d-alpha tocopherol), synthetic vitamin E (dl-alpha tocopherol) and mixtures thereof.

* * * * *